United States Patent [19]

Dziabo et al.

[11] Patent Number: 5,320,806
[45] Date of Patent: * Jun. 14, 1994

[54] METHODS TO DISINFECT CONTACT LENSES

[75] Inventors: Anthony J. Dziabo, El Toro; Paul S. Ripley, Irvine, both of Calif.

[73] Assignee: Allegan, Inc., Irvine, Calif.

[*] Notice: The portion of the term of this patent subsequent to Aug. 4, 2009 has been disclaimed.

[21] Appl. No.: 888,356

[22] Filed: May 22, 1992

Related U.S. Application Data

[60] Division of Ser. No. 592,558, Oct. 4, 1990, Pat. No. 5,135,623, which is a continuation-in-part of Ser. No. 461,540, Jan. 5, 1990, Pat. No. 4,997,626.

[51] Int. Cl.$^5$ .................... A61L 2/02; C25B 1/26
[52] U.S. Cl. .................... 422/29; 422/23; 422/297; 134/901; 204/101; 204/DIG. 6
[58] Field of Search .............. 22/22, 23, 28, 29, 292, 22/297; 134/901; 204/101, DIG. 6

[56] References Cited

U.S. PATENT DOCUMENTS

| | | | |
|---|---|---|---|
| Re. 32,672 | 5/1988 | Huth et al. | 252/95 |
| 3,278,447 | 10/1966 | McNicholas | 252/186.21 |
| 3,622,479 | 11/1971 | Schneider | 204/149 |
| 3,763,006 | 10/1973 | Callerame | 204/103 |
| 3,910,296 | 10/1975 | Karageozian et al. | 134/2 |
| 3,912,451 | 10/1975 | Gaglia, Jr. | 134/42 X |
| 4,084,747 | 3/1978 | Alliger | 239/4 |
| 4,104,190 | 8/1978 | Hartshorn | 252/95 X |
| 4,202,740 | 5/1980 | Stoner et al. | 422/22 X |
| 4,236,992 | 12/1980 | Themy | 204/278 |
| 4,361,471 | 11/1982 | Kosarek | 204/128 |
| 4,499,077 | 2/1985 | Stockel et al. | 424/149 |
| 4,557,925 | 12/1985 | Lindahl et al. | 424/19 |
| 4,568,517 | 2/1986 | Kaspar et al. | 422/30 |
| 4,614,549 | 7/1986 | Ogunbiyi et al. | 422/28 X |
| 4,654,208 | 3/1987 | Stockel et al. | 424/78 |
| 4,689,215 | 8/1987 | Ratcliff | 424/53 |
| 4,767,559 | 8/1988 | Kruse et al. | 252/106 |
| 4,997,626 | 3/1991 | Dziabo et al. | 422/37 |
| 5,078,908 | 1/1992 | Ripley et al. | 252/187.21 |

FOREIGN PATENT DOCUMENTS

| | | |
|---|---|---|
| 1156420 | 11/1983 | Canada . |
| 0082798 | 6/1983 | European Pat. Off. . |
| 0147100 | 7/1985 | European Pat. Off. . |
| 0196075 | 1/1986 | European Pat. Off. . |
| 0209071 | 1/1987 | European Pat. Off. . |
| 0255041A1 | 5/1988 | European Pat. Off. . |
| 0278224 | 8/1988 | European Pat. Off. . |
| 3626082A1 | 11/1988 | Fed. Rep. of Germany . |
| WO8504107 | 9/1985 | PCT Int'l Appl. . |
| WO8605695 | 10/1986 | PCT Int'l Appl. . |
| 2094992A | 9/1982 | United Kingdom . |
| 2151039A | 7/1984 | United Kingdom . |
| 2139260A | 11/1984 | United Kingdom . |
| 2173017A | 10/1986 | United Kingdom . |

OTHER PUBLICATIONS

Abstract:CA Selects: Controlled Release Technology; Issue 2, 1987; 106:9424f.
Eudragit L Data Sheet; Info L-2/e, published more than 1 year before filing date (prior art).
Stoner, et al. The Mechanism of Low Frequency a.c. Electrochemical Disinfection, *Bioelectrochemistry and Bioenergetics*, 9(1982) 229-243.

Primary Examiner—Robert J. Warden
Assistant Examiner—E. Leigh Dawson
Attorney, Agent, or Firm—Frank J. Uxa

[57] ABSTRACT

A method of disinfecting a contact lens is disclosed and comprises placing the contact lens to be disinfected into a liquid electrolyte containing chlorine dioxide precursor, e.g., stabilized chlorine dioxide, and forming a disinfecting amount of chlorine dioxide in the liquid electrolyte by passing an electric current through the liquid electrolyte.

19 Claims, 3 Drawing Sheets

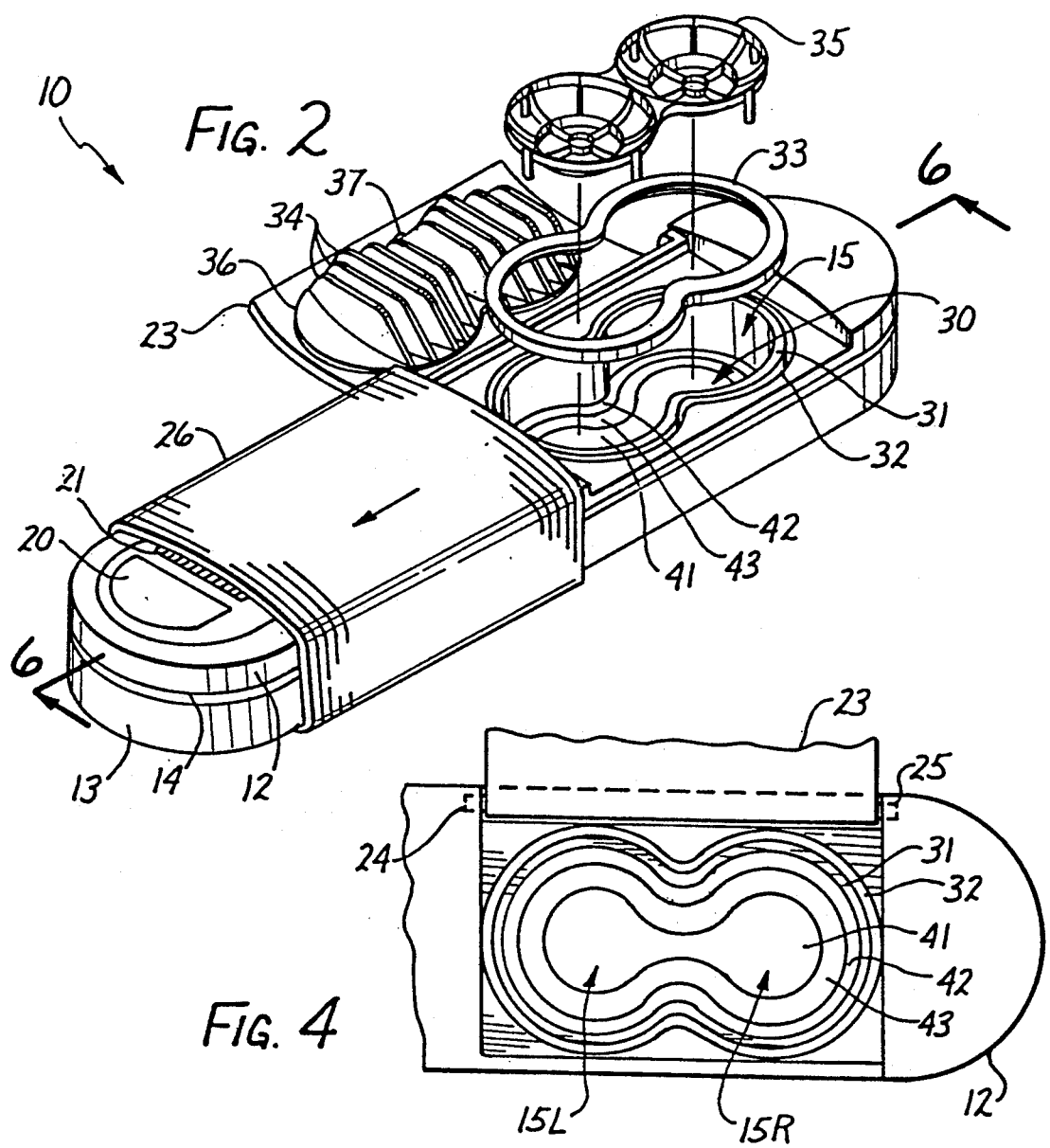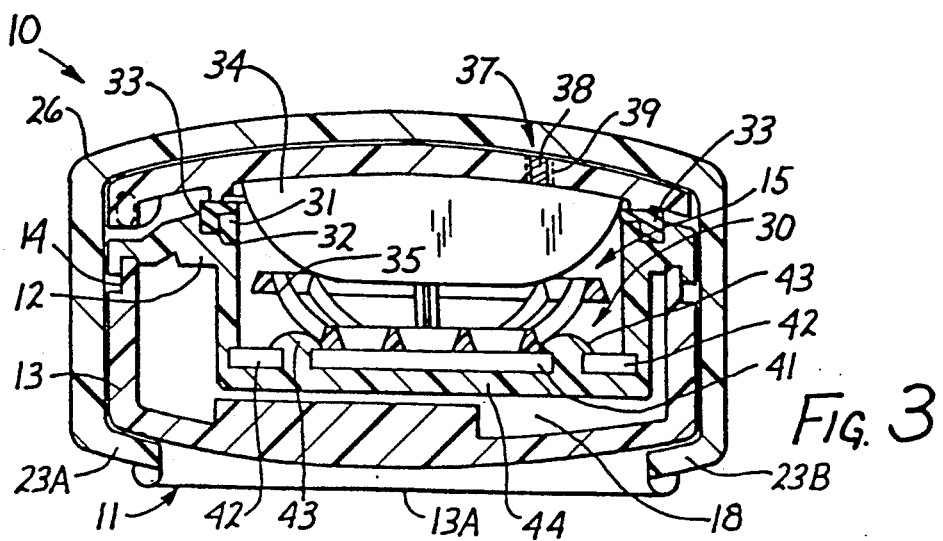

METHODS TO DISINFECT CONTACT LENSES

This application is a division of application ser. no. 592,558, filed Oct. 4, 1990, now U.S. Pat. No. 5,135,626.

BACKGROUND OF THE INVENTION

This invention relates to disinfecting lenses, such as contact lenses. In particular, the invention relates to methods useful to quickly and effectively disinfect contact lenses.

Contact lenses should be periodically disinfected to protect the wearer's eyes from infection and to improve the wearer's comfort. It is often desirable that lens disinfecting be accomplished quickly, e.g., for the convenience of the wearer. However, conventional fast-acting disinfectants that are used with contact lenses have a high potential to cause eye irritation. A disinfectant which can be easily and effectively dissipated after use would be advantageous to reduce the chance of eye irritation.

Stoner U.S. Pat. No. 4,202,740 and Tanaka, et al Canadian Pat. No. 1,156,420 disclose contact lens disinfection methods in which a contact lens is submerged in a saline solution subjected to electrolysis to produce chlorine, and possibly hypochlorous acid, to disinfect the contact lens. Although these materials do provide effective lens disinfection, they tend to linger in the solution and may cause eye irritation. Clearly, a new disinfection method involving an effective disinfectant which is rapidly dissipated would be advantageous.

SUMMARY OF THE INVENTION

New methods for disinfecting objects, such as lenses, and in particular contact lenses, have been discovered. These methods utilize a disinfecting amount of chlorine dioxide produced by electrolysis. Chlorine dioxide is a very effective disinfectant, e.g., for contact lenses. In addition, after the desired disinfecting has taken place, the produced chlorine dioxide rapidly dissipates, e.g., so as to reduce the chances of eye irritation when the disinfected contact lens is placed in the eye.

In one broad aspect, the invention involves a method for disinfecting an object, such as a lens, and in particular a contact lens. The object to be disinfected is placed into, preferably totally immersed in, a liquid electrolyte containing chlorine dioxide precursor. A disinfecting amount of chlorine dioxide is formed in the liquid electrolyte by passing an electric current through the liquid electrolyte. This produced chlorine dioxide preferably effectively disinfects the object. The electric current is stopped, preferably, after the disinfecting amount of chlorine dioxide is formed. After the disinfecting has taken place, the disinfected object is removed from the liquid electrolyte. For example, if a contact lens is disinfected, the disinfected contact lens is removed from the liquid electrolyte and may be placed directly in the eye. Alternately, a simple saline rinse and/or soak of the disinfected lens may be employed before placing the lens in the eye.

Overall, the present invention is very effective and easy to use. This encourages the lens wearer to disinfect his/her contact lenses frequently, resulting in more comfort and less eye irritation.

DETAILED DESCRIPTION OF THE INVENTION

The present system is applicable for disinfecting objects, including all types of lenses, and in particular contact lenses, which are benefited by disinfecting. Suitable lenses may be made of any material or combination of materials and may have any suitable configuration. Soft contact lenses are suitably disinfected in accordance with the present process.

One important feature of the present invention is the use of chlorine dioxide per se produced by electrolysis as the disinfectant. In order to provide for this chlorine dioxide production by electrolysis, a liquid electrolyte containing chlorine dioxide precursor is provided. Such precursors act in the liquid electrolyte in response to passing an electric current through the electrolyte to produce chlorine dioxide in a disinfecting amount, in particular a contact lens disinfecting amount. Chlorine dioxide per se and not, for example, a chlorine dioxide precursor, acts as the primary, preferably as the sole, disinfecting agent to disinfect the lens. As used herein, a disinfecting amount of chlorine dioxide means such an amount as will reduce the microbial burden or load by one log order in 3 hours or less, preferably in 1 hour or less, and more preferably in 10 minutes or less.

In general, the chlorine dioxide precursors useful in the present invention are those which form or produce chlorine dioxide in a liquid electrolyte, preferably a liquid aqueous electrolyte, in response to passing an electric current through the precursor-containing electrolyte.

Among the preferred chlorine dioxide precursors useful in the present invention are stabilized chlorine dioxide, chlorite components and mixtures thereof. The term "stabilized chlorine dioxide" as used herein means one or more chlorine dioxide-containing complexes and/or one or more chlorite-containing components and/or one or more other entities capable of forming chlorine dioxide in a liquid electrolyte in response to passing an electric current through the precursor-containing electrolyte.

Examples of such chlorite components include metal chlorites, and in particular alkali metal and alkaline earth metal chlorites. A specific example of a chlorite component which is useful as a chlorine dioxide precursor is technical grade sodium chlorite. Among the preferred chlorine dioxide-containing complexes are complexes of chlorine dioxide with carbonate, chlorine dioxide with bicarbonate and mixtures thereof. The exact chemical composition of many of the chlorine dioxide precursors, e.g., stabilized chlorine dioxide, and in particular the chlorine dioxide-containing complexes, is not completely understood. The manufacture or production of certain chlorine dioxide precursors is described in McNicholas U.S. Pat. No. 3,278,447, which is hereby incorporated in its entirety by reference herein. Specific examples of useful chlorine dioxide precursor sources include products such as that sold under the trademark Dura Klor by Rio Linda Chemical Company, Inc., and that sold under the trademark Anthium Dioxide by International Dioxide, Inc. An especially useful chlorine dioxide precursor source is a product sold under the trademark Purogene by Bio-Cide International, Inc. The chlorine dioxide precursor may be included in a liquid electrolyte at a predetermined concentration, e.g., a concentration chosen to provide a disinfecting amount of chlorine dioxide in response to passing an electric current through the precursor-containing electrolyte. Preferably, the liquid electrolyte has sufficient chlorine dioxide precursor so as to have a potential of producing chlorine dioxide in the range of about 0.002% to about 3%, more preferably about 40 ppm to about 1000 ppm by weight, based on the total weight of the liquid electrolyte including the chlorine dioxide precursor or precursors. Sufficient chlorine dioxide is preferably produced to provide a maximum concentration of at least about 2 ppm by weight of chlorine dioxide in the liquid electrolyte, more preferably about 2 ppm to about 100 ppm by weight of chlorine dioxide in the liquid electrolyte.

In one embodiment, the chlorine dioxide precursor includes a functionality selected from carbonate, borate, sulfate, phosphate, and mixtures thereof.

The liquid electrolyte used is selected to have no substantial detrimental effect on the object being treated and to allow, and preferably to even facilitate, the present disinfection treatment or treatments. The liquid electrolyte should have sufficient conductivity to allow the passage of the electric current. The liquid electrolyte is preferably aqueous-based. A particularly useful liquid aqueous medium is that derived from saline, e.g., a conventional saline solution.

The disinfecting preferably occurs at a temperature to maintain the liquid electrolyte substantially liquid. For example, when the liquid electrolyte is aqueous-based, it is preferred that the temperature be in the range of about 0° C. to about 100° C., and more preferably in the range of about 10° C. to about 60° C. Disinfecting at or about ambient temperature is very convenient and useful. The disinfecting preferably occurs at or about atmospheric pressure. The electric current is preferably passed through the chlorine dioxide precursor-containing liquid electrolyte for a period of time to produce sufficient chlorine dioxide to effectively disinfect the object being treated. Such times can be in the range of about 1 second to about 2 minutes or more, preferably about 3 seconds to about 30 seconds. Some additional time, e.g., on the order of about 10 seconds or less to about 20 minutes or more, may be useful after the electric current is stopped to allow for the disinfecting of the object, e.g., contact lens, to be completed.

The electric current which is passed through the liquid electrolyte can be generated from line voltage or from a storage battery. If line voltage is employed: it is preferred that the voltage be stepped down for safety considerations. An electric current generated from a storage battery is preferred. The current passed through the liquid electrolyte is preferably in the range of about 2 milliamperes to about 500 milliamperes, more preferably about 10 milliamperes to about 150 milliamperes.

In order to insure that the pH of the liquid aqueous-based electrolyte is maintained within the desired range during and/or following the disinfecting procedure, the liquid aqueous-based electrolyte may include at least one buffer component. Although any suitable buffer component may be employed, it is preferred to select such component so as not to substantially detrimentally affect the desired formation of chlorine dioxide. It is preferred that the buffer component be inorganic.

Among the preferred buffer components are those which include phosphate functionalities, borate functionalities, carbonate functionalities and mixtures thereof. Alkali metal and alkaline earth metal buffer components are advantageously used in the present invention. Sodium chloride may be employed to provide buffering action. The pH of the liquid aqueous-based electrolyte is preferably maintained in the range of about 6 to about 8, in particular after the passage of the electric current through the liquid electrolyte has ended.

After the disinfecting of the object is complete, the disinfected object is removed from the liquid electrolyte, and, often with little or no additional processing is ready for use. For example, if a contact lens is disinfected in accordance with the present invention, the disinfected lens is removed from the liquid electrolyte and may be placed directly in the lens wearer's eye for safe and comfortable wear. Alternately, a simple saline rinse and/or soak of the disinfected contact lens may be employed before the disinfected lens is placed in the wearer's eye.

Any suitable electrolysis cell may be employed. A particularly useful apparatus for practicing the present invention is illustrated in the drawings and described hereinbelow.

BRIEF DESCRIPTION OF THE DRAWINGS

FIG. 2 is a partially exploded perspective view showing details of the lens compartment of this apparatus.

FIG. 3 is an enlarged cross sectional view taken generally along line 3—3 of FIG. 1.

FIG. 4 is an enlarged plan view of a portion of this apparatus with the cover open to show the electrodes at the bottom of the lens compartment.

DETAILED DESCRIPTION OF THE DRAWINGS

Figure 1:
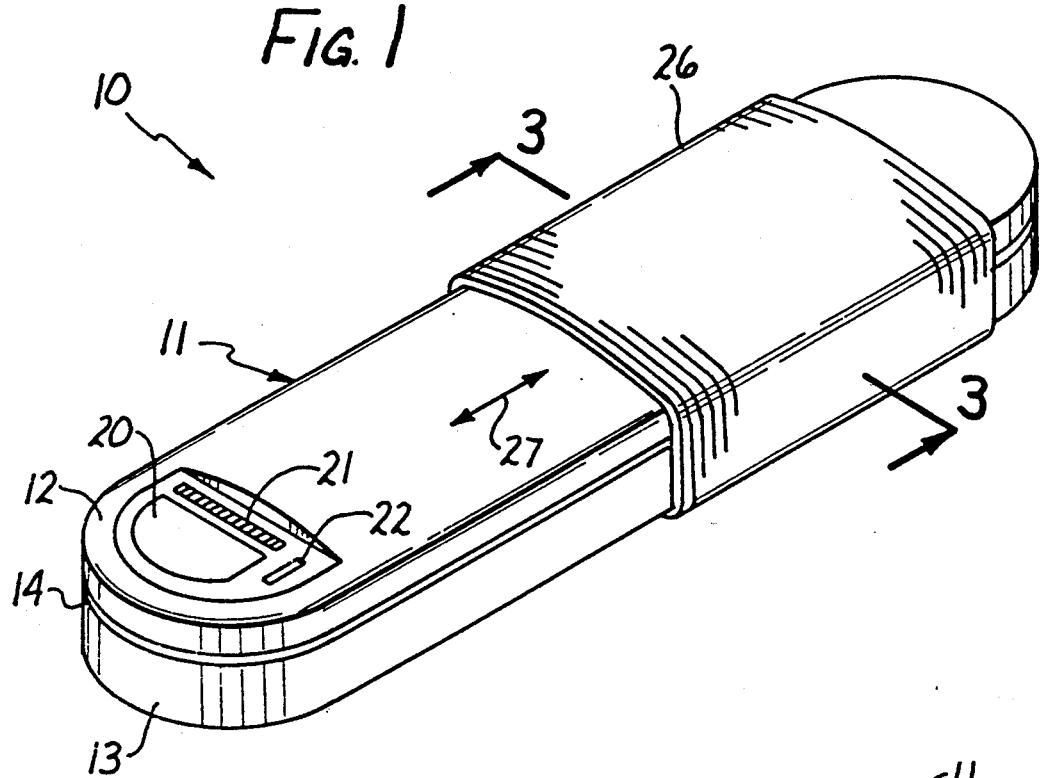
FIG. 1 is a perspective view of an electrolysis apparatus useful in carrying out the present invention.

Referring now to the drawings, and in particular FIGS. 1 and 2, an electrolysis apparatus, shown generally at 10, comprises a body or case 11 including an upper member or first portion 12 and a lower member or second portion 13 attached together along seam 14. The first and second portions 12 and 13 are of suitable composition, such as polystyrene, fabricated according to known techniques, such as injection molding, and they are bonded together or otherwise suitably attached along the seam 14.

Together they form the elongated, hand-held case 11 having a size and shape adapted to be grasped in the hand as a convenient combination carrying case and lens disinfecting apparatus. The illustrated embodiment is approximately eighteen centimeters long, four centimeters wide, and two centimeters deep, although these dimensions are not critical.

Figure 5:
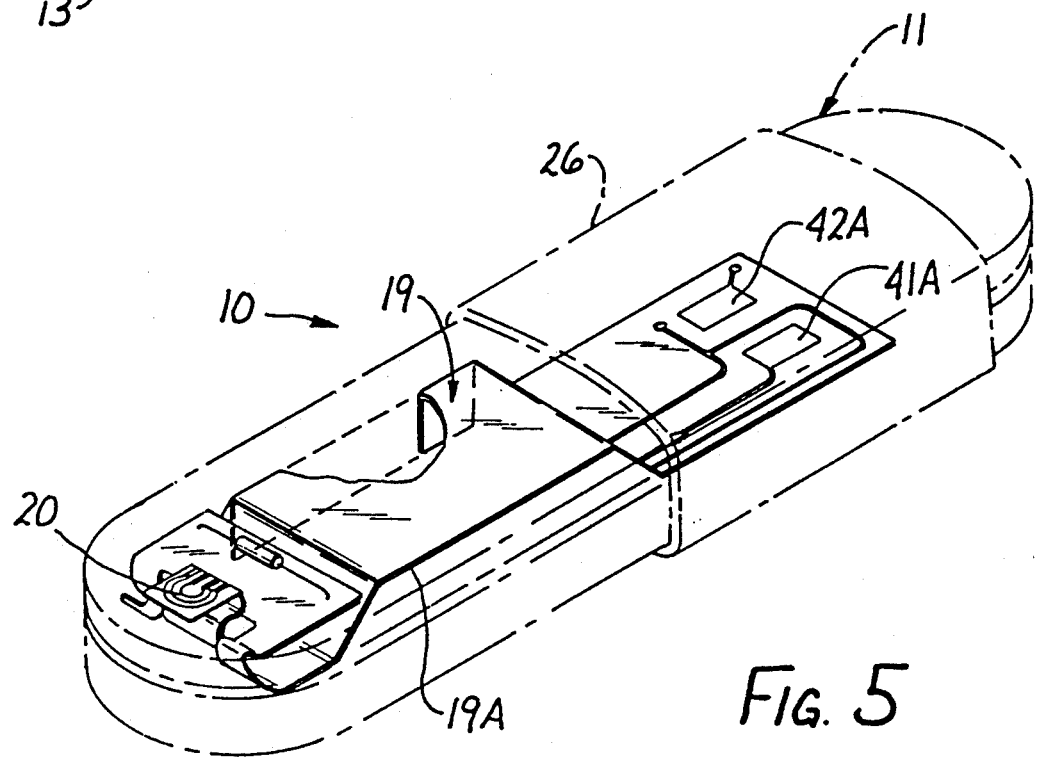
FIG. 5 is a perspective view of the membrane circuit board as it is mounted within the apparatus case (depicted in phantom lines).
Figure 6:
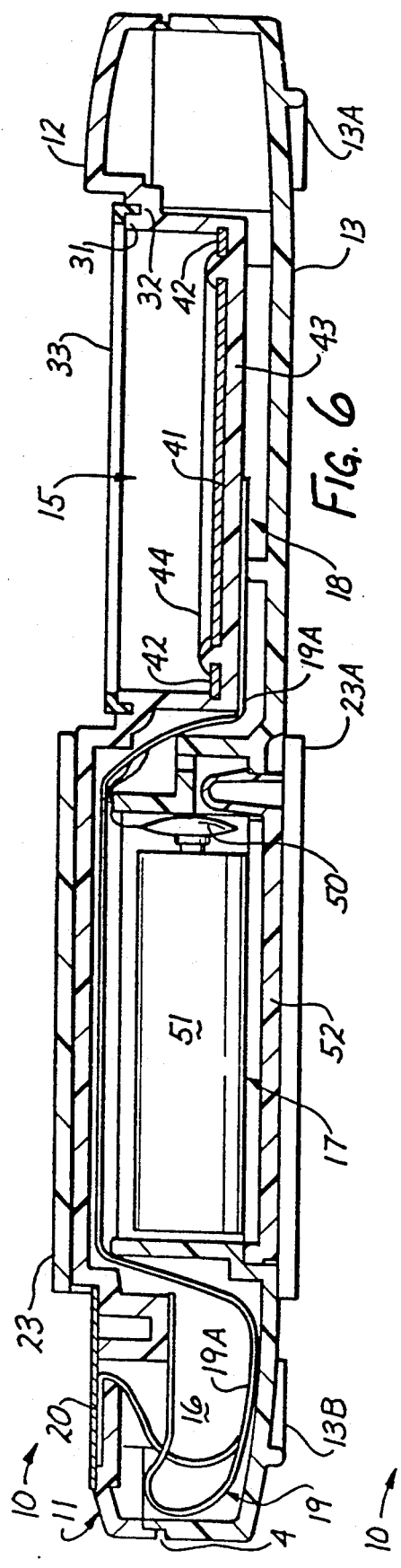
FIG. 6 is an enlarged cross sectional view of the apparatus taken generally along line 6—6 of FIG. 2.

The first portion 12 defines a first compartment or lens well 15 in which to contain a pair of contact lenses in a buffered aqueous solution containing 0.005% by weight (calculated as potential chlorine dioxide) of stabilized chlorine dioxide, such as the product sold by Bio-Cide International, Inc. under the trademark Purogene (FIGS. 3, 4 and 6). The second portion 13 defines a second compartment or power unit compartment including a rearward portion 16, an intermediate portion 17, and a forward portion 18 (FIG. 6) in which to contain a power unit 19. The power unit 19 employs a membrane circuit board 19A disposed within the rearward, intermediate, and forward portions 16–18 according to known techniques (FIGS. 5 and 6) to generate an electrical current that is supplied to the lens well 15.

Depressing the pushbutton switch 20 (FIG. 1) activates the power unit 19 for a period of time, preferably in the range of about 1 second to about 2 minutes and more preferably about 3 seconds to about 30 seconds. This results in a current, e.g. in the range of about 2 to about 500 milliamperes, preferably about 10 milliamperes to about 150 milliamperes and particularly about 80 milliamperes, being passed through the solution in lens well 15 to form chlorine dioxide in the solution in the lens well which disinfects the lenses in the lens well. First indicator 21 signals that a disinfecting cycle is in progress, and second indicator 22 signals a low battery condition.

A hinged cover member or cover 23 (FIG. 2) is used to cover the lens well 15. It is mounted on the case 11 by suitable means such as protrusions extending from the cover 23 (not shown) that fit in mating recesses 24 and 25 on the case 11 (FIG. 4). The cover 23 can be moved between an open position, such as illustrated in FIG. 2, and a closed position covering the lens well 15. Thus, only one cover need be manipulated, and operation is relatively easy.

For further ease of operation, the apparatus 10 includes a slidable retainer member or sleeve 26 to retain the cover member 23 in the closed position. The sleeve 26 has a size and shape adapted to fit over the exterior of the case 11 so that it can be slid back and forth in the direction of the arrow in FIG. 1 for this purpose. Of course other slidable arrangements can be utilized.

The sleeve 26 may be fabricated from a suitable thermoplastic composition injected molded to the desired configuration. The illustrated embodiment employs a resilient polyacetate composition that is dissimilar from the case 11, and this results in a low coefficient of friction between the case 11 and sleeve 26 so that the sleeve 26 operates all the more easily. The sleeve 26 is grasped with the fingers or hand and slid between a first position as illustrated in FIG. 2 that enables access to the lens well 15 and a second position as illustrated in FIG. 1 in which the cover member 23 is retained in the closed position.

Considering the lens well 15 in further detail, it is in the form of an upwardly opening compartment or chamber having a left section 15L and a right section 15R (FIG. 4). Each one of the sections 15L and 15R is shaped and dimensioned to contain a quantity of the above-noted solution and a lens immersed in the solution. As an idea of size, the sections 15L and 15R are each circularly-shaped with a diameter of approximately twenty-seven millimeters and a depth of approximately twelve millimeters, and they combine to form the single, figure-eight shaped lens well 15 illustrated. Thus, the solution can circulate freely between the two sections unimpeded for more effective disinfecting.

The lens well 15 extends from a lower portion 30 to a lip 31. The lip 31 circumscribes the lens well 15 to provide a surface facing the cover 23. The lip 31 is, in turn, circumscribed by a groove 32 that receives an elastomeric sealing member 33 composed of suitable material such as medical grade silicone rubber. The cover 23 includes a plurality of ribs 34 that are arranged to extend downwardly into the lens well 15 when the cover 23 is in the closed position, and so disposed. The ribs 34 act in retaining lenses (not shown) immersed in a solution placed in the lens well 15, within a lens basket 35.

The lenses are retained loosely so that they do not float on bubbles produced during electrolysis. They are not held tightly against the basket 35, which is fabricated of a suitable composition such as a medical grade polystyrene.

Referring to FIGS. 2, 3 and 4, when the cover 23 is moved to the closed position, a downwardly-extending ridge 36 on the cover 23 contacts the sealing member 33 in high-pressure-per-unit sealing engagement. This keeps solution from leaking out of the lens well 15 when the cover 23 is closed. A vent 37 in the cover 23 includes a filter element 38 disposed within a hole 39 in the cover 23 acts to provide for discharging gas from the lens well 15 while blocking passage of the solution. The filter element 38 may be a 0.22 micron hydrophobic filter of the type manufactured by Gelman Sciences of Ann Arbor Michigan. This element passes gas, but not liquid under less pressure than thirty pounds per square inch.

A pair of electrodes are disposed within the lens well 15. They include a first electrode 41 and a second electrode 42 which circumscribes circumscribing the first electrode. The first electrode 41 serves as an anode, and it is provided in the form of a relatively broad plate to increase the anode surface area at which electrolysis takes place. The second electrode 42 serves as the cathode. The electrodes 41 and 42 are separated by an electrically nonconductive isolating ring 43 that is part of the bottom 44 in which the electrodes are embedded. The composition of the first electrode 41 is titanium with a black surface coating of platinum group metal oxide, in particular ruthenium dioxide, about one micron thick. The second electrode 42 can be any corrosion resistent electrode material such as titanium or stainless steel. Other materials, e.g., metals, metal oxides and the like, may be employed in the first electrode 41 and/or second electrode 42 provided that such other material or materials are electrically compatible, are effective in the present system, are substantially resistant to the environment or environments to which such electrodes are exposed, and have no substantial detrimental effect on the disinfection process or on the objects, e.g., contact lenses, being disinfected. Such other materials include, for example carbon, nickel, silver, gold and the like.

The figure eight shape of the first electrode 41 is approximately fifteen millimeters in diameter at each of its loops. This provides increased surface area while protecting against current flow between the electrodes 41 and 42 over the isolating ring 43. This helps increase the rate at which electrolysis can proceed. Each one of the electrodes 41 and 42 is connected electrically to the power unit 19 by suitable means, such as a pair of electrically conductive terminals 41A and 42A (FIG., 5) on the membrane circuit board 19A.

Referring to FIG. 6, the power unit 19 includes a battery connector 50 with which to connect a nine-volt battery 51 to the power unit 19 as a source of electrical power. The battery 51 is placed in the intermediate portion 17, and a hinged battery compartment lid 52 is closed to secure the battery 51 in place.

Figure 7:
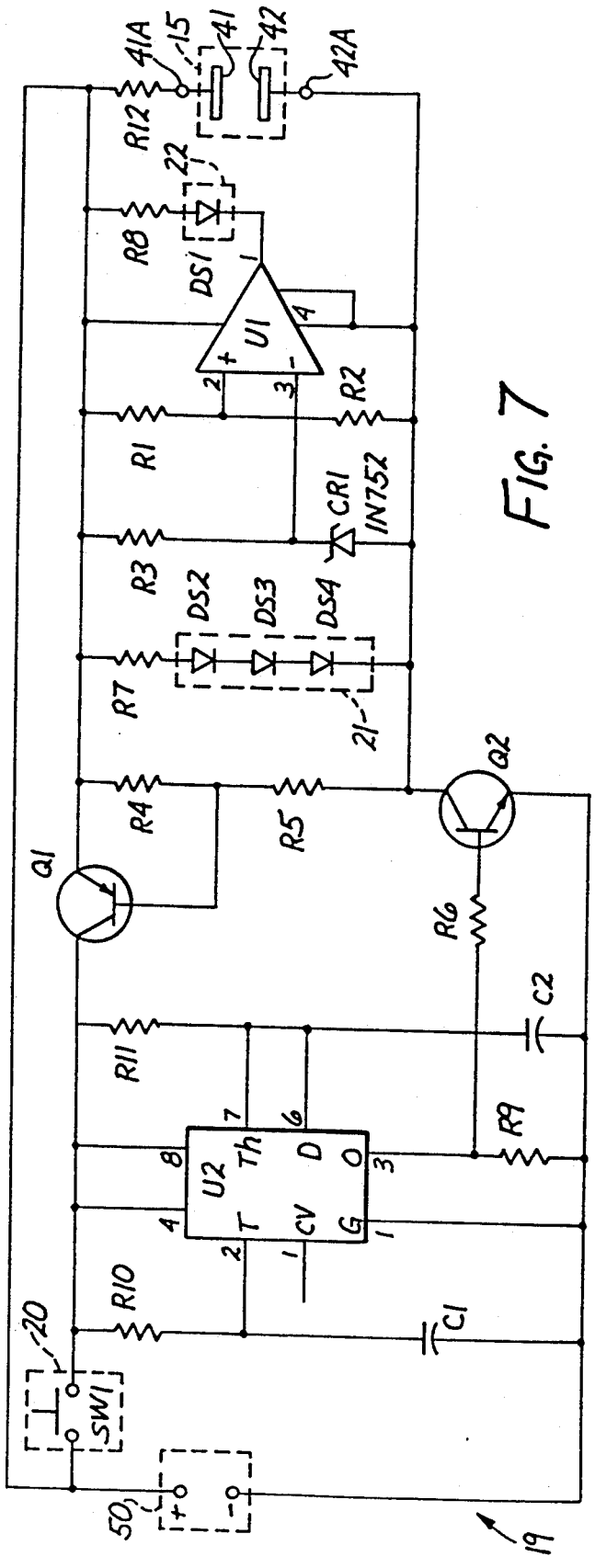
FIG. 7 is a schematic circuit diagram of the power supply unit employed in this apparatus.

The circuitry employed in the power unit 19 is shown in the schematic circuit diagram of FIG. 7. The membrane circuit board 19A is laced through the second compartment portions 16-18 as illustrated in FIG. 6 so that the switch 20, indicators 21 and 22, and electrodes 41 and 42 are electrically connected to the membrane circuit board 19A. These components and the battery connector 50 are enclosed in dashed lines in FIG. 7 to highlight their position.

When the switch 20 is depressed, power is supplied from the nine volt battery 51. The switch 20 is of the momentary-contact type, and depressing it causes current to be supplied to a timer integrated circuit U2 wired as a monostable multivibrator. The period of U2 is dependent upon the values of a resistor R11 and a capacitor C2. These are selected for a suitable disinfecting period they being in the illustrated apparatus 10 one megohm for resistor R11 and 10 microfarads for capacitor C2 with a type 555 timer integrated circuit.

When the timer U2 is triggered by depressing switch 20 to close SW1, the base of the NPN transistor Q2 is biased high by the output of timer U2. This causes transistor Q2 to turn 'on'. Through this action, the base of the PNP transistor Q1 is biased low, and switches 'on' to supply power to the time after SW1 is opened.

The transistor Q2 functions as a switch to perform several functions. First, it provides for a current return path to the battery 51 enabling the operation of other circuit components. Second, it illuminates the disinfection cycle LED indicators DS2, DS3 and DS4 (first indicator 21). Third, it permits current to flow through the lens well 15 and thus produce chlorine dioxide from the stabilized chlorine dioxide in the lens well. Fourth, it activates a type 311 comparator integrated circuit U1 wired as a voltage comparator, with a 1N752 zener diode CR1 providing a reference voltage of approximately 5.6 volts to the inverting input of the voltage comparator U1.

The positive voltage from the battery 51 is connected via the positive terminal on connector 50 to the noninverting input of the voltage comparator U1 through a resistor voltage divider including resistors R1 and R2. The comparator U1 is triggered by a battery voltage of less than about 7.5 volts. When this occurs, the output on pin 7 of the comparator U1 goes to ground potential and illuminates the low battery LED indicator DS1 (second indicator 22).

A current-limiting resistor R12 in series with the contact 41A leading to the first electrode 41, serves to limit the current to the lens well 15. Resistors R8 and R7 are current-limiting resistors in series with the LED indicators.

Preferably, the electrochemistry system of the invention utilizes a low voltage, more preferably in the range of about 2.1 to about 6.5 volts DC, at relatively high currents, more preferably in the range of about 10 to about 150, still more preferably about 50 to about 150 milliamperes, across the first and second electrodes 41 and 42 in a NaCl buffered aqueous solution containing 0.005% by weight of stabilized chlorine dioxide to produce chlorine dioxide and hydrogen. Sufficient buffer is present to maintain the pH of the solution in the range of about 6 to about 8 during the time chlorine dioxide is being formed.

The disinfecting cycle can be prolonged, if desired, by reducing the current level during the disinfecting cycle.

A brief description of the electrochemistry that takes place to produce chlorine dioxide from a chlorite component is as follows:

The oxidative half-reaction at the anode that occurs:

$$ClO_2^- \rightarrow ClO_2 + e^-$$

The reduction half-reaction at the cathode that occurs:

$$2H_2O + 2e^- \rightarrow H_2 + 2OH^-$$

Operationally, lenses to be disinfected may be first cleaned with a lens cleaner, e.g., an enzymatic lens cleaner.

In a particularly useful embodiment, the contact lens may be subjected to the action of at least one enzyme effective to remove debris from a contact lens. Among the types of debris that form on contact lens during normal use are protein-based debris, mucin-based debris, lipid-based debris and carbohydrate-based debris. One or more types of debris may be present on a single contact lens.

The enzyme employed may be selected from enzymes which are conventionally employed in the enzymatic cleaning of contact lenses. For example, many of the enzymes disclosed in Huth et. al. U.S. Pat. RE 32,672 and Karageozian et al U.S. Pat. No. 3,910,296 are useful in the present invention. Each of these patents is incorporated in its entirety by reference herein. Among the useful enzymes are those selected from proteolytic enzymes, lipases, carbohydrate-active enzymes, e.g., carbolytic enzymes, and mixtures thereof.

Preferred Proteolytic enzymes are those which are substantially free of sulfhydryl groups or disulfide bonds. Metallo-proteases, those enzymes which contain a divalent metal ion such as calcium, magnesium or zinc bound to the protein, may also be used.

A more preferred group of proteolytic enzymes are the serine proteases, particularly those derived from *Bacillus* and *Streptomyces* bacteria and *Asperigillus* molds. Within this grouping, the still more preferred enzymes are the derived alkaline proteases generically called subtilisin enzymes. Reference is made to Deayl, L., Moser, P.W. and Wildi. B.S., "Proteases of the Genus Bacillus. II Alkaline Proteases", Biotechnology and Bioengineering, Vol. XII, pp 213–249 (1970) and Keay, L. and Moser, P.W., "Differentiation of Alkaline Proteases form Bacillus Species" Biochemical and Biophysical Research Comm., Vol 34, No. 5, pp 600–604, (1969).

The subtilisin enzymes are broken down onto two subclasses, subtilisin A and subtilisin B. In the subtilisin A there are enzymes derived from such species as *B. subtilis, B. licheniformis* and *B. pumilis.* Organisms in this sub-class produce little or no neutral protease or amylase. The subtilisin B sub-class is made up of enzymes from such organisms a *B. subtilis, B. subtilis var. amylosacchariticus, B. amyloliquefaciens* and *B. subtilis* NRRL B3411. These organisms produce neutral proteases and amylases on a level about comparable to their alkaline protease production. One or more enzymes from the subtilisin A sub-class are particularly useful.

In addition other preferred enzymes are, for example, pancreatin, trypsin, collaginase, keratinase, carboxylase, aminopeptidase, elastase, and aspergillo-peptidase A and B, pronase E (from *S. griseus*) and dispase (from *Bacillus polymyxa*).

If such an enzyme or enzymes are employed, an effective amount is preferably used. Such amount will be that amount which effects removal in a reasonable time (for example overnight) of substantially all of at least one type of debris from a lens due to normal wear. This standard is stated with reference to contact lens wearers with a history of normal pattern of lens debris accretion, not the very small group who may at one time or another have a significantly increased rate of debris accretion such that cleaning is recommended every day, or every two or three days.

The amount of enzyme required to make an effective cleaner will depend on several factors, including the inherent activity of the enzyme, and the extent of its interaction with the hydrogen peroxide present.

As a basic yardstick, the working solution should contain sufficient enzyme to provide about 0.001 to about 3 Anson units of activity, proferably about 0.01 to about 1 Anson units, per single lens treatment. Higher or lower amounts may be used.

Enzyme activity is pH dependent so for any given enzyme, there is a particular pH range in which that enzyme will function best. The determination of such range can readily be done by known techniques.

After cleaning, the lens or lenses are rinsed with saline solution to remove residual enzyme, and then placed into the lens well with about 8 milliliters of buffered saline solution. The cover is closed and the retainer slid along the case to secure the door.

The disinfection cycle is activated to cause a desired current to pass through the electrolyte solution for a desired period of time, to produce the desired amount of chlorine dioxide and effectively disinfect the lenses. At the end of the cycle, the lenses can be removed from the electrolysis cell. The lenses are preferably then rinsed with an appropriate saline solution and are ready to be worn.

The present disinfecting methods provide for easy, rapid and safe contact lens disinfection. Chlorine dioxide, which is produced by electrolysis, is a very effective contact lens disinfecting agent. The use of chlorine dioxide to disinfect contact lenses provides substantial advantages, e.g., in terms of effectiveness, safety and ease of dissipation, relative to, for example, chlorine and hypochlorous acid which are formed by electrolysis of a saline solution. The use of chlorine dioxide precursors, in particular stabilized chlorine dioxide, is a very effective way of providing "potential" chlorine dioxide to the electrolysis cell. After disinfection, the produced chlorine dioxide quickly dissipates, thus reducing or eliminating the need for post-disinfecting processing, e.g., rinsing and/or soaking the disinfected lens, before the disinfected lens can be safely and comfortably worn.

While this invention has been described with respect to various specific examples and embodiments, it is to be understood that the invention is not limited, thereto and that it can be variously practiced within the scope of the following claims.

What is claimed is:

1. A method of disinfecting an object comprising:
   placing an object into a liquid electrolyte containing chlorine dioxide precursor; and
   forming a disinfecting amount of chlorine dioxide in said liquid electrolyte containing said object by passing an electric current through said liquid electrolyte.

2. The method of claim 1 wherein said chlorine dioxide precursor is selected from the group consisting of stabilized chlorine dioxide, chlorite components and mixtures thereof.

3. The method of claim 1 wherein said liquid electrolyte is aqueous-based.

4. The method of claim 1 wherein said chlorine dioxide precursor is initially present in said liquid electrolyte containing said object to be disinfected in an amount in the range of about 0.002% to about 3% by weight, calculated as potential chlorine dioxide.

5. The method of claim 1 wherein said chlorine dioxide precursor is selected from the group consisting of chlorite components and mixtures thereof.

6. The method of claim 1 wherein said chlorine dioxide precursor is selected from the group consisting of chlorine dioxide-containing complexes and mixtures thereof.

7. The method of claim 1 wherein said electric current is in the range of about 2 milliamperes to about 500 milliamperes.

8. The method of claim 1 wherein said electric current is passed for a period of time in the range of about 1 second to about 2 minutes.

9. The method of claim 8 wherein said period of time is in the range of about 3 seconds to about 30 seconds.

10. The method of claim 1 which further comprises removing said object from said liquid electrolyte.

11. The method of claim 1 wherein said object is an ophthalmic device.

12. A method of producing a disinfectant comprising:
    providing an aqueous-based liquid electrolyte containing chlorine dioxide precursor; and
    forming chlorine dioxide in said aqueous-based liquid electrolyte in the presence of an object to be disinfected in an amount effective to disinfect said object to be disinfected by passing for a period of time an electric current through said aqueous-based liquid electrolyte.

13. The method of claim 12 wherein said chlorine dioxide precursor is selected from the group consisting of stabilized chlorine dioxide, chlorite components and mixtures thereof.

14. The method of claim 12 wherein said chlorine dioxide precursor is initially present in said aqueous-based liquid electrolyte in the presence of said object to be disinfected in an amount in the range of about 40 to about 1000 ppm by weight, calculated as potential chlorine dioxide.

15. The method of claim 12 wherein said aqueous-based liquid electrolyte includes at least one buffer component.

16. The method of claim 12 wherein said electric current is in the range of about 10 milliamperes to about 150 milliamperes.

17. A method of producing a disinfectant comprising:
    providing an aqueous-based liquid electrolyte containing a buffer component and chlorine dioxide precursor selected from the group consisting of stabilized chlorine dioxide, chlorite components and mixtures thereof, said chlorine dioxide precursor being present in an amount in the range of about 50 ppm to about 1000 by weight, calculated as potential chlorine dioxide; and
    passing an electric current through said aqueous-based liquid electrolyte in the presence of an object to be disinfected at conditions and for a period of time effective to form chlorine dioxide in said aqueous-based liquid electrolyte in an amount sufficient to effectively disinfect said object to be disinfected.

18. The method of claim 17 wherein said electric current is in the range of about 10 milliamperes to about 150 milliamperes, and said period of time is in the range of about 3 seconds to about 30 seconds.

19. The method of claim 18 wherein said buffer component is present in an amount effective to maintain the pH of said aqueous-based liquid electrolyte in the range of about 6 to about 8 during said passing step.

* * * * *

UNITED STATES PATENT AND TRADEMARK OFFICE
CERTIFICATE OF CORRECTION

PATENT NO. : 5,320,806
DATED : June 14, 1994
INVENTOR(S) : Dziabo et al

It is certified that error appears in the above-indentified patent and that said Letters Patent is hereby corrected as shown below:

Column 8, line 5; delete "$2e^{(3)}$" and insert in place thereof --$2e^-$--.

Column 9, line 68; delete "to be disinfected".

Signed and Sealed this

Twenty-fifth Day of April, 1995

Attest:

BRUCE LEHMAN

Attesting Officer     Commissioner of Patents and Trademarks